United States Patent [19]

Pader

[11] 4,435,380

[45] Mar. 6, 1984

[54] HUMECTANTS FOR CLEAR GEL DENTIFRICE COMPOSITIONS

[75] Inventor: Morton Pader, Teaneck, N.J.

[73] Assignee: Lever Brothers Company, New York, N.Y.

[21] Appl. No.: 485,913

[22] Filed: Apr. 18, 1983

Related U.S. Application Data

[63] Continuation-in-part of Ser. No. 344,238, Jan. 29, 1982, abandoned.

[51] Int. Cl.$^3$ ............................................. A61K 7/16
[52] U.S. Cl. ........................................ 424/49; 424/361
[58] Field of Search ....................................... 424/49-58

[56] References Cited

U.S. PATENT DOCUMENTS

| | | | |
|---|---|---|---|
| 3,538,230 | 11/1970 | Pader et al. | 424/50 |
| 3,842,167 | 10/1974 | Block | 424/49 |
| 3,906,090 | 9/1975 | Colodney | 424/52 |
| 4,357,314 | 11/1982 | Lynch | 424/49 |

FOREIGN PATENT DOCUMENTS

| | | |
|---|---|---|
| 2008853 | 2/1971 | Fed. Rep. of Germany . |
| 40-15120 | 7/1965 | Japan . |
| 620828 | 12/1980 | Switzerland . |
| 1062283 | 3/1967 | United Kingdom . |
| 1169538 | 11/1969 | United Kingdom . |
| 4932171 | 10/1971 | United Kingdom . |
| 1336944 | 11/1973 | United Kingdom . |
| 2100983 | 1/1983 | United Kingdom . |

OTHER PUBLICATIONS

Frostell, Odont. Revy 24, 217 (1973), pp. 217–226.

*Primary Examiner*—Shep K. Rose
*Attorney, Agent, or Firm*—Milton L. Honig; James J. Farrell

[57] ABSTRACT

A visually clear dentifrice composition comprising about 20 to 70% by weight of humectant solids, about 5 to 50% by weight of an abrasive, and water,
(a) the humectant solids comprising a hydrogenated hydrolyzed polysaccharide wherein said hydrogenated hydrolyzed polysaccharide contains 25% or less maltitol and at least about 30% by weight of oligosaccharides with at least three glucose units;
(b) said abrasive being capable of:
 (i) cleaning and polishing human teeth without damaging said teeth, and of
 (ii) forming a clear gel when combined with the humectant system,
(c) the amount of water and the distribution of the molecular weights of said hydrogenated hydrolyzed polysaccharide being such as to render the dentifrice composition translucent or transparent.

23 Claims, No Drawings

HUMECTANTS FOR CLEAR GEL DENTIFRICE COMPOSITIONS

This application is a continuation-in-part of co-pending application Serial No. 344,238, filed Jan. 29, 1982, abandoned.

BACKGROUND OF THE INVENTION

The present invention relates to dentifrice compositions and especially to clear gel toothpastes.

Dentifrice compositions for promoting the health and appearance of the mouth, and especially of the teeth and gums, are well known. Until recently, these compositions were usually in the form of opaque toothpastes.

Such compositions generally contain agents for cleaning and polishing the teeth. Cleaning, as this word is used in the dentifrice art, refers to the removal of food debris, dental plaque, calculus, tooth surface stains, etc. Polishing refers to the creation of a smooth tooth surface. Typically, these cleaning and polishing agents are abrasives. Abrasives that have been used in opaque dentifrice compositions include calcium carbonate, dicalcium phosphates, tricalcium phosphate, calcium pyrophosphate and analogous water-insoluble magnesium salts.

In addition to abrasives, toothpastes usually contain additional ingredients which serve a variety of purposes. Some examples of such additional ingredients include binders, thickeners, preservatives, sweeteners, colorants, flavors, surfactants, buffers, germicides, antibiotics, astringents and fluorine compounds.

Toothpastes can be dispensed from a variety of containers, such as deformable plastic bottles and aerosol cans. However, they are generally dispensed from collapsible aluminum tubes or collapsible tubes consisting of laminates comprising aluminum. Caps are placed on these tubes in order to protect the product during distribution and to prevent the toothpaste from drying out due to evaporation of water or other volatile materials during use by the consumer A problem that can arise with such systems is the cementing of the cap to the tube during use of the product by the consumer. This can occur, for example, when toothpaste unintentionally gets onto the threads of the tube and the tube is left undisturbed for a long period of time. This problem is called cap lock and is due to the crystallization of solid material in the toothpaste. In order to prevent cap lock, humectants are added to toothpastes in order to preserve moisture and prevent crystallization.

A related problem is caused by the tendency of some consumers not to replace the cap between uses. The paste in the nozzle of the tube can dry out if precautions are not taken, i.e., if appropriate humectants are not present in the toothpaste in effective amounts.

Sorbitol, glycerine, and mixtures thereof are examples of humectants commonly used in toothpaste compositions. Sorbitol is a sugar alcohol which is generally made by completely hydrolyzing starch and hydrogenating the purified dextrose syrup derived therefrom. The starch may be derived from any convenient source, such as from corn, potatoes, rice or wheat. Most dextrose syrups made in the United States are obtained by hydrolyzing corn starch. In Europe, it is not uncommon to obtain dextrose syrups from potato starch.

Recently, toothpastes in the form of clear gels have been developed; see Pader et al, U.S. Pat. No. 3,538,230 (Lever Brothers Company), Colodney, U.S. Pat. No. 3,906,090 (Colgate-Palmolive Co.) and Wason, U.S. Pat. No. 4,272,509 (J. M. Huber Corporation). Clear gel toothpastes have proved to be very popular with consumers. Undoubtedly, this is due at least in part to their appealing translucent appearance and surprisingly pleasant taste.

The method for assessing translucency in this invention involves use of a standard chart consisting of black symbols varying in size on a white background. This is the RIT Alphanumeric Resolution Test Object, RT 4-74, produced by Graphic Arts Research Center, Rochester Institute of Technology. The ability to discern the symbols clearly through a sample of product of standard thickness is measured. The symbols are assigned numbers from $-12$ to $+13$. The higher, more positive the number, the greater the clarity. The method can be applied to measurement of translucency of toothpaste. If even the most prominent symbol cannot be readily defined through the layer of toothpaste, the toothpaste is considered cloudy and not translucent. In the practice of this invention, products with a numerical rating of about $-12$ or higher are considered translucent.

Difficulties arise in formulating clear gel toothpastes. This is because the abrasives that have generally been used in opaque toothpastes cannot be rendered translucent or transparent. Only materials with the correct combination of abrasive, organoleptic and optical properties are suitable for use as abrasives in clear toothpastes. Certain silica xerogels, precipitates and aluminosilicate salts have been found to have these requisite properties. Silica xerogels and aluminosilicate salts are described in U.S. Pat. Nos. 3,538,230 and 3,906,090, respectively. Silica precipitates are described in U.S. Pat. No. 4,272,509. Silica xerogels are most preferred in this invention, and silica precipitates are also preferred.

It has been demonstrated that translucency or transparency can be obtained when the refractive index of the humectant system is adjusted so as approximately to coincide with the refractive index of the abrasives. For example, it is stated in U.S. Pat. No. 3,906,090 that a sodium aluminosilicate abrasive having a refractive index of about 1.45 to 1.46 forms a clear gel toothpaste when combined with a gel or liquid vehicle having a refractive index of about 1.44 to 1.47. When conventional humectants such as glycerine and sorbitol are employed, the refractive indices of the abrasive and humectant system must be very close to each other for the degree of clarity equal to that defined above to be obtained. A difference in refractive index of, say, more than about 0.02 units at 25° C. would result in clarity less than the minimum defined by the current invention as determined by the method described below.

Sorbitol is often employed as a humectant in clear gel toothpastes. A 70% by weight aqueous solution of sorbitol has a refractive index of 1.46, which is similar to that of the commonly used abrasives for clear or translucent dentifrices. Also, sorbitol has the advantage of being an effective and essentially non-cariogenic sweetener.

Sorbitol, however, is not a sufficiently effective humectant to prevent cap lock completely or to completely inhibit drying out when the silica abrasive dentifrice is exposed to the atmosphere. As a result, glycerine is often admixed with sorbitol. Glycerine's refractive index of 1.47 is similar to that of a 70% solution of sorbitol, which is 1.46. Thus, a mixture of glycerine and 70% sorbitol solution does not have a refractive index substantially different from that of 70% sorbitol alone. Since glycerine adds the humectancy which sorbitol lacks, a mixture of 70% aqueous sorbitol and glycerine is a good humectant for clear gel toothpastes containing either aluminosilicate, precipitated silica or silica xerogel abrasives.

When 70% aqueous sorbitol and/or glycerine comprise the humectant system in a clear gel dentifrice, the index of refraction of the humectant system must closely approximate that of the abrasive in order to establish and maintain the transparency of the dentifrice composition. As a result of this limitation, the amount of water that can be present is severely limited since the presence of water lowers the refractive index of the humectant system while the refractive index of the abrasive remains essentially constant. Therefore, the level of sorbitol and glycerine must remain relatively high. High levels of glycerine are undesirable because of high and rapidly increasing cost. A considerable cost reduction would be effected if a way were found to replace at least some of the glycerine with water in clear gel dentifrice compositions. Likewise, it would be desirable to similarly replace part or all of the sorbitol.

A method for lowering the cost of raw materials which are used as humectants in toothpaste is disclosed in co-assigned U.S. Pat. No. 3,842,167 to Block et al. This patent suggests the replacement of part of the glycerol and/or sorbitol humectant system with aqueous solutions of maltodextrins. Maltodextrins are starch hydrolyzates wherein the saccharides contain substantial amounts of di-, oligo- and polysaccharides. Maltodextrins are normally made by the partial hydrolysis of starch. Such materials are unsuited for use as the sole humectant in toothpastes. As noted in U.S. Pat. No. 3,842,167, these materials could be used as only part of the humectant system. Moreover, maltodextrins are fermentable by cariogenic bacteria, while sorbitol and glycerine are essentially nonfermentable by these bacteria.

Suggestions have been made to add hydrogenated hydrolyzed starch other than sorbitol to opaque dentifrice compositions. Japanese Patent Publication No. 15120/1965 (Towa Kasei Kogyo KK) discloses the addition of a syrup containing 60 to 90% maltitol as a humectant in toothpaste. Maltitol is a sugar substitute obtained by hydrogenating the disaccharide maltose.

U.K. Pat. No. 1,336,944 (Unilever Ltd.) discloses that hydrogenated hydrolyzed starch products described in U.K. Pat. Nos. 1,062,283 and 1,169,538 (Lyckeby Starkelseforadling AB) may be added to opaque toothpaste as sweetening agents. The Lyckeby patents are directed to non-cariogenic sweeteners for candy. These sweeteners, which are marketed under the trade name Lycasin by Roquette Freres, France, are hydrogenation products of mixed mono- and polysaccharides obtained by partially hydrolyzing starch. It is important to note that the requirements for a sweetener in hard candy are different from those of a humectant in toothpaste. In hard candy applications, it is only necessary that the sweetener does not crystallize. In toothpaste applications, on the other hand, it is necessary that the humectant remains non-crystalline and fluid so that the toothpaste will be flowable when subjected to a slight pressure during extrusion from its container.

In U.S. Pat. No. 4,357,314 (ICI Americas, Inc.) hydrogenated maltose containing starch hydrolyzate syrups were disclosed as humectants useful for the preparation of clear transparent gel toothpastes. High maltitol (25–94%) and low sorbitol (5–30%) content characterize these syrups. Maltitol was claimed as the essential component providing humectancy and imparting transparency to the dentifrice gel.

Similar hydrogenated starch hydrolyzates were described in Swiss Pat. No. 620,828 (Gaba AG). Transparent toothpastes were said to be obtainable with a hydrogenated starch hydrolyzate commercially available under the mark "Polysorb 80/55". Again, these hydrolyzates were distinguished by a high maltitol content. The excellent humectancy and clarity retention were specifically ascribed to the presence of maltitol.

As noted in the ICI Americas and Swiss patents, there are cost advantages to using hydrogenated starch hydrolyzates of high maltitol content over glycerol and/or sorbitol. Yet, even these materials are expensive to produce. Manufacture of high maltitol hydrolyzates such as "Polysorb 80/55" and "Lycasin" materials demand partial, very controlled hydrolysis and care in hydrogenation. Special enzymes or bacterial organisms, whose reaction environments must be carefully controlled, are required for the hydrolysis step. Hydrogenation must also be carefully monitored so as to avoid further hydrolysis and not to exceed dextrose equivalent values generally less than 15%. Specifically, special procedures must be used to obtain hydrolyzates with high maltose content. Process specifications for materials such as "Lycasin" are described in British Pat. No. 1,169,538 (Lyckeby Starkelseforadling AG). Bacterial and enzymatic processes for hydrolysis of starch are also reported in German Pat. No. 2,008,853 (Roquette Freres). Discovery of less costly humectants would be an especially welcome advance in this art.

There is a need, therefore, for an effective humectant system suitable for use in a clear gel toothpaste wherein part or all of the glycerine and/or sorbitol can be replaced and wherein there is less of a requirement that the abrasive system and the humectant system have closely matched refractive indices, permitting thereby more water to be present than would otherwise be possible in a clear paste. There is also a need for humectant materials for use in clear gel toothpaste which are less costly to prepare than glycerine, sorbitol or high maltitol content hydrogenated starch hydrolyzate. These substitutes should be sweet, available from a wide variety of starting materials, and not critically dependent on having a specific chemical composition.

A second problem in formulating clear gel dentifrices is that of providing proper texture. Upon extrusion from the tube a dentifrice should retain body. Too frequently, however, the extruded segment slumps. There is poor cohesion. From its perch atop the brush, the paste rapidly spreads forth drooping down into the bristles. Clear gel dentifrices containing humectants with substantial maltitol content suffer from a slumping problem no less severe than equivalent dentifrices made with sorbitol or sorbitol and glycerine.

Relatedly, elegant toothpastes are expected to break sharply upon extrusion from the tube. The ribbon should not string out; it should have shortness of texture. Unlike conventional opaque dentifrices, clear gel dentifrices generally do string out. Inadequate shortness is related to the relatively small amounts (about 25%) of abrasives present in clear gels compared with the 40–50% abrasive content in conventional, opaque dentifrices.

In U.S. Pat. No. 3,689,637, a method is described whereby improved shortness of texture is obtained by incorporating polyethylene glycol of appropriate molecular weight into the dentifrice. Although ameliorative of the problem, polyethylene glycol does not achieve the same shortness of texture as observed with a conventional high-abrasive dentifrice. This solution is also costly. The instant invention successfully addresses this problem.

OBJECTS OF THE INVENTION

It is, therefore, an object of the invention to provide a humectant system suitable for use in a clear gel abrasive-containing toothpaste.

A second object of the present invention is to provide a humectant system for a clear gel toothpaste which contains materials other than (but not necessarily exclusive of) sorbitol, maltitol and glycerine.

It is a further object of the present invention to provide a humectant system which permits the amount of water to be increased in a clear gel dentifrice composition when compared with humectant systems consisting mainly of a 70% aqueous sorbitol solution with or without glycerine.

Yet another object of the present invention is to provide a method for treating the gums and teeth of human beings with a clear gel toothpaste containing a humectant system other than aqueous sorbitol, glycerine and/or high maltitol content hydrogenated starch hydrolyzate.

Still another object of the present invention is to provide a clear gel dentifrice with texture superior to that previously available.

Finally, it is an object of the present invention to provide a humectant system less costly than those hitherto known.

SUMMARY OF THE INVENTION

These and other objects of the present invention have been obtained by providing a visually clear dentifrice composition comprising about 20 to 70% by weight of humectant solids, about 5 to 50% by weight of an abrasive, and water,
(a) the humectant solids comprising a hydrogenated hydrolyzed polysaccharide wherein said hydrogenated hydrolyzed polysaccharide contains 25% or less maltitol and at least about 30% by weight of oligosaccharides with at least three glucose units;
(b) said abrasive being capable of:
 (i) cleaning and polishing human teeth without damaging said teeth, and of
 (ii) forming a clear gel when combined with the humectant system,
(c) the amount of water and the distribution of the molecular weights of said hydrogenated hydrolyzed polysaccharide being such as to render the dentifrice composition translucent or transparent.

Also provided is a method of cleaning and polishing teeth comprising treating said teeth with a visually clear dentifrice composition comprising about 20 to 70% by weight of humectant solids, about 5 to 50% by weight of an abrasive, and water,
(a) the humectant solids comprising a hydrogenated hydrolyzed polysaccharide wherein said hydrogenated hydrolyzed polysaccharide contains 25% or less maltitol and at least about 30% by weight of oligosaccharides with at least three glucose units;
(b) said abrasive being capable of:
 (i) cleaning and polishing human teeth without damaging said teeth, and of
 (ii) forming a clear gel when combined with the humectant system,
(c) the amount of water and the distribution of the molecular weights of said hydrogenated hydrolyzed polysaccharide being such as to render the dentifrice composition translucent or transparent.

DETAILED DESCRIPTION OF THE INVENTION

The dentifrice composition of the present invention is a clear gel toothpaste. By clear is meant having a translucency reading of about −12 or higher as the term translucency reading has been defined above, i.e., using RIT Alphanumeric Resolution Test Object RT4-74. The term "gel" as used herein includes not only those compositions which are gels in the strict technical sense but also gel-like compositions which have the same feeling and appearance of gels. Gel-like materials would include, for example, the pastes and creams which are familiar in the toothpaste art.

The toothpastes of the present invention comprise about 40 to 90% by weight of a humectant system and about 10 to 60% by weight of non-humectants. Humectants comprise two or more portions, about 55 to 80% by weight of a solid portion and about 20 to 45% by weight of an aqueous liquid portion in the simplest systems and additionally glycerine and/or other liquids in more complex systems. The humectant solids useful in the present invention are low maltitol hydrogenated hydrolyzed polysaccharides referred to as polyols. Low maltitol hydrogenated hydrolyzed polysaccharides can conveniently be prepared by hydrolyzing a polysaccharide consisting of chains of glucose residues and hydrogenating the resulting hydrolyzate.

Methods for hydrolyzing polysaccharides are well known. Any suitable method may be used in the preparation of the humectants presently described. For example, a polysaccharide may be hydrolyzed by means of acid catalysis. Such a method is described in Conrad, U.S. Pat. No. 3,329,507. The description of polysaccharide hydrolysis in U.S. Pat. No. 3,329,507 is incorporated herein by reference.

The complete hydrolysis of polysaccharides useful in this invention leads to glucose or dextrose. The polysaccharides which lead to the inventive humectants are not, however, completely hydrolyzed. The polysaccharides are only partially hydrolyzed to a solution rich in trisaccharides and higher oligosaccharides. Oligosaccharides refer herein to saccharides which contain 3 or more glucose units per molecule.

Polyols are analyzed by High Pressure Liquid Chromatography (HPLC). It has become common to refer to the composition of polyols in terms of DP fractions. Thus, $DP_1$ refers to sorbitol and mannitol, $DP_2$ refers to maltitol and any other disaccharide materials that associate with it, $DP_3$ refers to oligosaccharides with 3 glucose units, and so forth. The DP values describe compositions in terms that are not complicated by the presence of isomers, e.g., $DP_2$ may be maltitol and isomaltitol.

In the present invention, the hydrolysis of the polysaccharide is terminated when at least about 30%, preferably about 40% but most preferably about 50% by weight of the mixture of saccharides is in the form of oligosaccharides. Preferably, the hydrolyzate will contain less than 40% $DP_1$ and $DP_2$ (glucose and maltose), no more than 25% $DP_2$ (maltose), about 30 to 40% $DP_3$ through $DP_9$ (oligosaccharides with 3-9 units) and 20-30% $DP_{10}$ or higher (oligosaccharides with over 9 glucose units). Of course, these percentages assume that subsequent hydrogenation does not substantially alter the proportions of the various saccharides from what they were prior to hydrogenation, e.g., by hydrolytic reactions during hydrogenation. Following hydrolysis, the mixture of monosaccharide, disaccharide and oligosaccharide is hydrogenated. The hydrogenation of saccharides is well known in the art. Such hydrogenation is usually catalyzed by nickel.

The hydrogenation of partially hydrolyzed polysaccharides is described in U.S. Pat. No. 3,329,507 and in U.K. Pat. Nos. 1,062,283 and 1,169,538. The description of these hydrogenations is incorporated by reference herein. The hydrolysis step is regulated and controlled so that the desired amount of oligosaccharides is formed. The hydrogenation step is usually conducted under conditions which do not lead to further hydrolysis or to hydrogenolysis of the oligosaccharides. Therefore, the percentages of hydrogenated oligosaccharides present in the syrup is substantially the same as the percentages of oligosaccharides present in the original hydrolyzate.

Any suitable source of polysaccharides may be used to provide the feed stock for the hydrolysis and hydrogenation steps. The source of the polysaccharides may be starch or cellulose. Starch is the preferred source.

Any source of starch may be used to provide the polysaccharide of the present invention. Suitable sources of starch include corn, potato, rice, and wheat. For reasons of availability, the preferred source of starch in the United States is corn and the preferred source of starch in Europe is corn or potatoes.

A number of advantages become apparent when the hydrogenated saccharide mixture in the toothpaste composition contains at least the minimum amount of hydrogenated oligosaccharides presently claimed. For one, hydrogenated oligosaccharides are good humectants in toothpaste compositions and the use of other humectants, such as glycerine and propylene glycol are neither necessary nor desirable. Thus, the present dentifrice compositions can be formulated with substantially no glycerine or humectant other than low maltitol hydrogenated oligosaccharides.

Neither sorbitol nor maltitol are necessary to the present dentifrice compositions, although it is usually not practical to prepare polyols totally free of them in the practice of this invention. Sorbitol and maltitol impart undesirable properties to clear gel dentifrices when used by themselves. Moreover, translucent dentifrice compositions comprising sorbitol as primary or sole humectant are not realized unless the refractive index of the aqueous humectant system and the abrasive system are relatively closely matched.

It has also unexpectedly been found that in dentifrices of the current invention greater clarity is obtained when the product obtained by hydrogenation of a hydrolyzate contains low amounts of sorbitol. This is apparent from Tables I and II below and especially samples numbers 1, 4, and 5.

It has also very unexpectedly been found that substantial amounts of sorbitol may be present provided that the sorbitol is added to hydrogenated oligosaccharide prepared from a hydrolyzate which yields upon hydrogenation only a small amount of sorbitol and a large amount of hydrogenated oligosaccharides.

It is evident that the critical feature of the polyols of this invention is that, used with the silica abrasives, they must contain a substantial proportion of hydrogenated oligosaccharides. These polyols are best obtained by hydrogenating hydrolyzates which yield a minimum of sorbitol. Hydrolyzates which yield on hydrogenation a major amount of sorbitol tend not to contain sufficient proportions of those oligosaccharides which provide the benefits of this invention. In other words, the presence of a low amount of sorbitol is an indication that the hydrogenation product contains sufficient oligosaccharides of sufficient quality so that the clarity of the toothpaste is promoted. It is theorized that the oligosaccharides of sufficient quality are those with at least three glucose units ($DP_3$ or higher). Therefore, the amount of sorbitol in the mixture of polyols obtained on hydrogenation should preferably be no more than about 25%.

The preferred polyol of this invention will contain less than about 40% $DP_1$ and $DP_2$ (sorbitol and maltitol), no more than 25% $DP_2$ (maltitol), about 30 to 40% $DP_3$ through $DP_9$ (oligosaccharides with 3-9 units) and about 20 to 30% $DP_{10}$ or higher (oligosaccharides with 10 or more units).

A further advantage of the claimed humectants is due to the higher viscosity provided by oligosaccharides than mono- or disaccharides. The viscosity increases as the molecular weight of the oligosaccharide increases. A sufficient amount of sufficiently high molecular weight hydrogenated oligosaccharides can replace, either in whole or in part, the customary thickeners used in toothpastes. Such customary thickeners include sodium carboxymethylcellulose, alginates, vinylcarboxy polymers, and xanthan gum. To the extent that the need for these expensive thickeners is reduced by use of the hydrogenated oligosaccharides, the cost of the dentifrice composition decreases.

It has also been found that the use of hydrogenated oligosaccharides obviates the requirement that the abrasive system closely match the refractive index of the humectant system, and vice versa. Thus, one can be more flexible in formulating a clear toothpaste containing hydrogenated oligosaccharides than a clear toothpaste containing hydrogenated mono- or disaccharides. This flexibility allows the amount of hydrogenated mono-, di- and oligosaccharides to decrease and the amount of water to increase while still maintaining the requisite translucency. The ability to use more water further reduces the cost resulting from the use of hydrogenated oligosaccharides in the humectant system.

The use of oligosaccharides in dentifrice compositions leads to cost saving in yet another way. The hydrolysis of the polysaccharide is a partial hydrolysis. A partial hydrolysis requires less time and less energy than a total hydrolysis. Therefore, the partial hydrolysis, which leads to the oligosaccharides useful in the presently described compositions, is less expensive to conduct than the more complete hydrolysis required to prepare mono- or disaccharides.

Another major advantage of the humectants disclosed herein is their ability to impart cohesion and shortness of texture to clear gels. Normally, a stringy tail attaches to segments of clear gel toothpaste extruded from a tube. Clear gels are especially vulnerable to stringiness because of their high humectant content. Consumers view stringiness as aesthetically unpleasing. They have come to expect sharp-breaking paste such as provided by conventional high-abrasive dentifrices. Unexpectedly, it has been found that use of low maltitol hydrogenated oligosaccharides affords clear gel dentifrices with texture equal in shortness to that of conventional dentifrices. This advantage is apparent whether the dentifrices are opaque, transparent or translucent. It is seen with all dentifrice systems containing high percentages of humectants and that depend on other mucilagenous materials such as gums for structure and binding water. Sorbitol and/or maltitol play no role in the effect. Only the higher hydrogenated polyols contribute to the phenomena.

Toothpastes must also exhibit cohesion. Once meted from the tube onto a brush, the paste should remain rigid. Slumping pastes will droop between the brush bristles. Not only is a slumping paste inelegant, much of the material will not arrive at the tooth surface. Clear gel dentifrices containing humectants with more than 25% maltitol and correspondingly lower amounts of oligosaccharide exhibit considerably more slumping than do those with the oligosaccharides of this invention.

An important concern in selecting polyols for use in this invention is that the content of higher oligosaccharides not be too high. The viscosity of the hydrogenated polysaccharide is related to that of the hydrolyzate from which it is derived. In the extreme, for example, an unhydrolyzed starch might be hydrogenated. The resultant product would yield too thick a dentifrice if used alone, and therefore would not be a good humectant. The product could be used in conjunction with major amounts of conventional humectants such as aqueous sorbitol or the like, but there is little advantage in doing so. In the practice of this invention, therefore, at least partial hydrolysis of the source polysaccharide prior to hydrogenation is necessary.

The degree of hydrolysis of a polysaccharide may be measured by the dextrose equivalent. The dextrose equivalent is defined as the amount of reducing sugars calculated as dextrose and expressed on a dry substance basis; see Kirk and Othmer, editors, "Encyclopedia of Chemical Technology", 2nd Edition, Volume 4, page 76. The dextrose equivalent of the hydrolyzates useful in the present dentifrices is about 15 to 85, preferably about 20 to 70, more preferably about 25 to 65 and most preferably 45 to 60.

It should be pointed out that it is within the scope of this invention to mix hydrolyzed starches prior to or after hydrogenation to achieve the content of hydrogenated oligosaccharides that is effective in this invention. By such admixture a wide range of distributions of sorbitol, maltitol and higher polyols can be obtained. The presence and amount below about 25% each of the sorbitol and/or maltitol is unimportant so long as the content of the higher polyols is high enough to achieve the objectives of this invention. Simply stated, the main concern is to provide a sufficient amount of higher polyols; once that is provided, the amount up to about 25% each of sorbitol and/or maltitol present has no detrimental effect, and their role is simply that of another humectant material, yielding some sweetness, body and solids content to maintain refractive index.

The amount of humectant solids present in the dentifrice compositions is an amount effective to prevent or at least substantially to resist the drying out of the dentifrice during normal storage and use. At the same time, the amount of the humectant solids is calculated to yield a dentifrice composition which is conveniently extruded from a tube and yields a ribbon which is firm and stable for a sufficient period of time when the dentifrice is placed on a toothbrush prior to use. The amount of humectant that is used to formulate the toothpaste depends on the amount of other materials present, such as abrasive silica, silica thickening agent, gums, glycerine, polyethylene glycol, propylene glycol and therapeutic agents. A maximum amount generally will be about 70% humectant solids. In general, about 20 to 70% by weight, preferably 30 to 60% by weight based on the total composition is an effective amount of humectant solids in the present dentifrice compositions.

The amount of humectant solids will also depend in part on the average number of glucose units in the oligosaccharide. The larger the number of glucose units, (i.e., the lower the dextrose equivalent), the lower the amount of humectant solids that will be required to form a toothpaste which can be conveniently extruded from a tube as a ribbon which retains integrity for a reasonable period of time on a toothbrush. It is understood that the amount of humectant solids needed to establish toothpaste structure is secondary to the need to have present a proper amount of water to provide clarity.

The most important non-humectant component in toothpastes are abrasives. The abrasives useful in the dentifrice compositions presently disclosed must have certain characteristics. The principal characteristics necessary are high cleaning and polishing ability, ability to form a clear gel, and safety for use in the mouth. Any abrasive possessing these three characteristics may be combined with the humectant in the present invention.

The abrasives must be able to penetrate and remove stain and debris from on and around the tooth without harming the enamel surface of the tooth, the tooth dentin, or the adjacent soft tissues under normal conditions of tooth brushing in order to be considered safe. Finally, the abrasive must be capable of forming a composition with a translucency rating of at least $-12$ when combined with the humectants disclosed and claimed herein.

Other important parameters which should be considered in choosing solid cleaning and polishing agents for dentifrices are compatibility with common dentifrice ingredients, such as thickening agents, foaming agents, etc., and compatability with therapeutic agents which might be incorporated into the dentifrice, for example, germicides, fluorides and the like. A still further common requirement is cosmetic acceptability. The abrasive must not impart either visual or organoleptic properties which detract from cosmetic acceptability. For example, the particle size must not be so large as to make the dentifrice feel unduly gritty in the mouth.

Abrasives which are especially useful in clear dentifrices are the silica xerogels described in Pader et al, U.S. Pat. No. 3,538,230. In fact, silica xerogels are the abrasives of choice for use in clear dentifrices and are the preferred abrasives in the present invention. Silica xerogels yield dentifrice compositions which result in surprisingly good cleaning and polishing characteristics when applied topically to the teeth. In addition, silica xerogels produce a high luster without excessive enamel or dentin abrasion. These silicas are also highly compatible with most common dentifrice ingredients, including oral health agents, and may be formulated to produce transparent or translucent pastes.

More specifically, the silica xerogels useful in the present dentifrice compositions are synthetic, amorphous, porous silica xerogels having an average particle diameter in the range from about 2 to about 30 microns and preferably in the range from about 3 to about 15 microns.

The silica xerogels are generally present in the composition in an amount sufficient to give the dentifrice a dentin abrasion value of at least about 15 units as measured by the dentin abrasion test described in the Pader et al patent discussed above. The description of the dentin abrasion test in the Pader et al patent, U.S. Pat. No. 3,538,230, is incorporated by reference herein. It should be understood, however, that toothpastes with dentin abrasion values below about 15 units are still encompassed by this invention.

As described in the Pader et al patent, the silica xerogels of the present invention may be prepared by the addition of a mineral acid to a sodium silicate solution to form a silica hydrogel. Hydrogels contain a three dimensional network of polymerized silica units. Several different types of silica gels can be made from the hydrogel depending, among other factors, on the conditions of drying or, generally, the type of water displacement in the initial gel.

In the preparation of the xerogels within the scope of the present invention, the initial hydrogel is washed and water is removed until the xerogel structure is established. Water can be removed, for example, by subjecting the hydrogel to a current of heated air.

During the removal of water, a shrinkage of the network's structure occurs reducing the average pore diameter. This microporous structure is the reason for the large surface area of the xerogel. The small size of the pores also contribute to the overall rigidity of xerogel particles making them ideal abrasives.

Further description of the silica xerogel useful in the present dentifrice composition and of its method of preparation is contained in Pader et al, U.S. Pat. No. 3,538,230. The description of the silica xerogels in the Pader et al patent and of its method of preparation is incorporated by reference herein.

Silica xerogels suitable for use in clear dentifrice compositions are commercially available. One suitable xerogel is marketed under the trade name Syloid 63. This material has an average particle diameter of about 8 to 10 microns.

Other suitable silicas include Syloid 65, which has an average particle diameter of about 5 microns; Syloid 73, which has an average particle diameter of about 5 microns and Syloid 404 which has an average particle diameter of about 6 microns. All of the above silica xerogels in the Syloid series are available from W. R. Grace, Davison Chemical Division.

Another class of abrasive materials suitable for use in the present dentifrice composition is the class of silicas known as precipitated silicas. Those precipitated silicas that are applicable are, in broadest terms, prepared by the admixture of a mineral acid and sodium silicate solution to form a precipitate followed by washing, drying and milling of the precipitate. The products are amorphous, hard particles which can be made with differing degrees of abrasivity. One such precipitated silica is disclosed by Wason, U.S. Pat. No. 4,272,509. Another type of precipitated silica which can be used, but which has only limited abrasive properties, is disclosed by Watson, U.S. Pat. No. 3,864,470. The description of precipitated silicas and the methods of their preparation disclosed in U.S. Pat. Nos. 4,272,509 and 3,864,470 are incorporated herein by reference.

The amount of abrasive is limited to those amounts which safely provide good polishing and cleaning and which, when combined with common toothpaste ingredients of a non-abrasive nature, will give a smooth, flowable, not excessively gritty, acceptable tasting toothpaste. This amount generally lies in the range of about 5% to about 50% by weight of the total dentifrice. The preferred range is from about 6 to about 35% and the most preferred range is about 7 to about 25% by weight of the dentifrice. Amounts greater than those mentioned above can yield a paste which is excessively firm and even rigid. Such pastes are difficult to package, to extrude and to use on a toothbrush. Amounts less than those contemplated, on the other hand, fail to furnish the desired polishing and cleaning.

In order to maintain the proper texture and thixotropic behavior as well as other desirable cosmetic properties, the dentifrice compositions of this invention may contain, in addition to the above-described essential cleaning and polishing agents, a second, less effective cleaning and polishing ingredient. For example, from about 0.5% to about 20% and preferably from about 2% to about 13% by weight of the dentifrice of a synthetic amorphous porous silica aerogel, a pyrogenic silica or a precipitated amorphous silica may be added to the silica xerogels. These optional abrasives polish but clean only to a limited degree when used alone. Typical examples include CaboSil, which is a pyrogenic silica from Cabot Corporation, Syloid 244 which is an aerogel, and Zeofree 153, a precipitated silica from J. M. Huber Corporation.

The amount of water present in the compositions is any amount which leads to transparent or translucent compositions. For economic reasons, the preferred amount of water is the maximum possible. Generally, the amount of water present in these compositions is at least about 10% by weight, preferably about 36% by weight, and most preferably about 50% by weight. For example, 10 to 50%, 12 to 36% and 15 to 30% are suitable amounts of water.

In toothpastes containing the humectants and abrasives as described above, water may be present in an amount which causes the refractive index of the liquid portion of the dentifrice composition to be significantly different from the refractive index of the abrasive. Even in these cases, the toothpastes are acceptably translucent. In toothpastes containing aqueous sorbitol or glycerine as the humectant with silica abrasives, however, the refractive indices of the abrasive and humectant must be very close if the toothpaste is to be translucent. Thus, for example, significant loss of translucency occurs in a silica dentifrice containing a humectant comprising 30% water and 70% sorbitol by weight of the humectant if the water content is increased from 30% to 40% by weight and the sorbitol content is decreased from 70 to 60% by weight. On the other hand, clarity is maintained within the limits of this invention when the water content of a silica dentifrice comprising 70% of the polyol of this invention as humectant is similarly increased; compare sample 1 with samples 2 and 3.

For example, the translucency reading of a 60% sorbitol/silica xerogel dentifrice was less than −12 (not translucent). The translucency reading of a comparable dentifrice with a 60% polyol humectant of this invention was −12, sufficiently within acceptable clarity. This difference in clarity is unexpected since the respective refractive indices of the 60% solutions are very close, viz., 1.438 and 1.446, respectively, at 25° C. (Compare sample numbers 1 and 2 in Tables I and II.).

Very unexpectedly it has been found that at a concentration of 70%, the concentration at which sorbitol is conventionally used as a dentifrice humectant, the humectants of this invention can yield substantially clearer pastes than sorbitol despite little difference in refractive index. Thus, for example, as seen in Tables I and II, a 70% sorbitol solution (Sample No. 1) with a refractive index of 1.459 gave a clarity reading of −9 when incorporated into a standardized toothpaste formulation, while a 70% solution of Sample No. 2 with a refractive index of 1.468 gave a clarity reading of +2 in the same formulation. Also compare sample numbers 1 and 3.

The reason for these findings is not readily apparent. Without being restricted by theory, it is proposed that the reason for the observed effects may be explained in the following terms:

The preparation of a translucent dentifrice based on an amorphous silica abrasive requires that the refractive index of the silica and of the humectant be very close. This pertains, however, to the refractive index of the humectant as it exists in the dentifrice, not as it exists prior to being incorporated into the dentifrice.

In accordance with my hypothesis, it is envisioned that the silica abrasive particle is a porous structure with finite-sized pores and reactive surfaces. Each particle is permeable to water and small molecules, but large molecules are excluded. It is further envisaged that when the silica particles are contacted with an aqueous polyol solution, as in the manufacture of a dentifrice, water and lower molecular weight polyols (sorbitol and maltitol, for example) freely enter into the porous silica, wherein water is bound by the silica. When the humectant is aqueous sorbitol and/or glycerine, the equilibrium established between the porous silica particles and the external humectant phase is governed by the fact that there is a free interchange of water and low molecular weight polyol (e.g., sorbitol) between the internal and external liquid phases of the silica particles. When a large amount of water is added, the refractive index of internal and external liquid phases is the same, and different from that of the silica. The result is loss of clarity of the total system. When the external phase comprises a proportion of higher hydrogenated oligosaccharides, however, a different situation prevails. These higher hydrogenated oligosaccharides tend to be excluded from the pores of the silica particles. They have the ability to bind relatively large amounts of water. In so doing, they alter the equilibrium hydration state of the silica as well as the composition of the internal phase of the silica particles. An equilibrium is established between the internal and external phases of the silica particle which is dissimilar to that realized with the conventional 70% sorbitol humectant. One consequence is a change in the apparent optical properties of the silica particles. An unexpected result of this change is better agreement in refractive index between the hydrated silica particle and its internal aqueous phase on one hand and the external liquid medium on the other. This better agreement leads to greater clarity. Addition of further water disrupts the equilibrium, but relatively large amounts of water must be added before it is disrupted so far as to yield a cloudy toothpaste.

Additional ingredients may be added to the toothpaste composition for a variety of purposes. Suitable additional ingredients include: binders such as sodium carboxymethylcellulose, alginates, and xanthan gum; thickeners, such as fumed silicas, polyethylene glycols and carboxyvinyl polymers; preservatives, such as benzoate and benzoic acid derivatives; sweeteners, such as saccharin, cyclamate and Acesulfam K; colorants, such as FD&C dyes, D&C dyes and pigments; flavors, such as peppermint, spearmint and cinnamon; surfactants, such as sodium lauryl sulfate, sodium lauroyl sarcosinate and others listed in Accepted Dental Therapeutics; buffers, such as phosphates, acetates and citrates; germicides, such as tribromsalicylanilide and benzalkoniuim chloride; antibiotics, such as penicillin and neomycin; astringents, such as zinc chloride and aluminum salts; and fluoride compounds, such as sodium fluoride, sodium monofluorophospate, stannous fluoride, and organic fluorides.

Having generally described the invention, a more complete understanding could be obtained by reference to certain specific examples which are provided herein for purposes of illustration only and are not intended to limit the claims unless otherwise specified.

EXAMPLE 1

Several polyols, obtained by hydrogenation of various corn starch hydrolyzates, were characterized. The data are presented in Table 1. Sample No. 1 was obtained as a commercially available material made by the hydrogenation of glucose syrup. The other samples were prepared from corn starch hydrolyzates with or without the addition of 70% sorbitol syrup (commercial). The hydrogenated saccharide distribution was determined by high pressure liquid chromatography. It will be seen that the refractive indices of all the samples were quite close.

EXAMPLE 2

Dentifrices were prepared utilizing the polyol preparations. A standard formulation was used, consisting of:

|  | Percent |
|---|---|
| Silica xerogel[1] | 14.0 |
| Silica aerogel[2] | 9.5 |
| Polyol + Water | 73.0 |
| Sodium carboxymethyl cellulose | 0.4 |
| Sodium benzoate | 0.1 |
| Sodium lauryl sulfate | 1.6 |
| Ethyl alcohol[3] | 2.1 |
|  | 100.7[3] |

[1]Syloid 63, from W. R. Grace Co., Davison Chemical Division
[2]Syloid 244, from W.R. Grace Co., Davison Chemical Division
[3]Approximately one-third of the alcohol is lost during processing of the toothpaste.

The sodium carboxymethylcellulose and the sodium benzoate was dispersed in about 90% of the polyol+water. The silicas were added and thoroughly mixed in. The sodium lauryl sulfate was dissolved in the remainder of the polyol+water, along with the alcohol. This solution was added to the paste mixture slowly to avoid excessive foaming, while mixing slowly. The total preparation was then warmed in a 50° C. oven several hours, and subjected to vacuum to remove the air. About one-third of the alcohol was removed in the deaeration process, but only a few tenths percent of water. The paste was cooled, packed into tubes, and stored at least about 1 week at ambient room temperatures. The clarity of the paste was then determined as described in Example 6.

The results are given in Table II. It may be seen that clarity was not clearly related to the refractive index of the polyol humectant solution.

EXAMPLE 3

The preparation of Example 2 was repeated, with Sample 3 except that a precipitated silica replaced the silica xerogel and the silica aerogel. The precipitated silica was Zeo 49, from W. M. Huber Corp. Clarity readings with 70% and 60% polyol solutions were −1 and −11, respectively, thereby showing that the polyols of this invention can also be applied to clear dentifrices comprising a precipitated amorphous silica abrasive material.

EXAMPLE 4

The effect of adding other materials commonly used in the manufacture of translucent dentifrices was tested, viz. polyethylene glycol, whose refractive index is close to that of silicas. The formulas of Example 2 and 3 were used, except that approximately 5 parts polyethylene glycol 400 was incorporated into 100 parts of toothpaste. Clarity readings with silica xerogel and silica precipitate, at 60% polyol/40% water in the humectant, were −12 and −12, respectively.

EXAMPLE 5

The translucency was assayed as follows:

A Teflon gasket for a 1½ inch beveled seat sanitary pipe is flattened to a height of 7/32 inch, care being used to insure the uniformity and flatness of the upper and lower surfaces. The ring is placed on a smooth clear glass plate, 3 inches square and 3/32 inch thick and is filled with toothpaste just to overflowing. A second, identical glass plate is pressed onto the toothpaste and the toothpaste is examined to ascertain the absence of air bubbles. The plates are placed on the RIT Alphanumeric Test Object, RT 4-74, and a translucency reading is taken by visual inspection.

TABLE I

| Sample No. | (1) | (2) | (3) | (4) | (5) |
|---|---|---|---|---|---|
| Analysis (Solids basis) | | | | | |
| Sorbitol | 97% | 3% | 10% | 78% | 58% |
| Mannitol | 3 | — | — | 2 | 1 |
| Maltitol(+isomaltitol) | — | 25 | 9 | 16 | 14 |
| Maltotriol | — | 10 | 6 | 3 | 1 |
| Higher polyols | — | 62 | 75 | 1 | 26 |
| Refractive Index at 25° C. | | | | | |
| 50% Solids | 1.418 | 1.425 | 1.424 | 1.418 | 1.419 |
| 60% Solids | 1.438 | 1.446 | 1.445 | 1.439 | 1.441 |
| 70% Solids | 1.459 | 1.468 | 1.465 | 1.460 | 1.462 |

TABLE II

| | Clarity reading at: | |
|---|---|---|
| Sample No. | 70% polyol solution | 60% polyol solution |
| 1 | −9 | Cloudy* |
| 2 | +2 | −12 |
| 3 | −2 | −12 |
| 4 | −8 | Cloudy |
| 5 | −9 | Cloudy |

*Cloudy indicates a reading of less than about −12.

EXAMPLE 6

Superior structural properties distinguish dentifrices containing the polyols of this invention from that of previously known humectants. Shortness of texture and high cohesion are two properties defining a desirable structure. Although shortness is easily apparent, it is difficult to quantify. Cohesion, however, may be measured.

Dentifrice Cohesion Test

The apparatus consists of a round 1 13/16-inch diameter brass base plate mounted with a perforated sleeve serving as the dentifrice sample holder. A similarly sized flat metal disk held by a hook is suspended above the perforated disk. The hook is attached to a Chatillon spring gauge actuated by a mechanized worm gear. The worm gear is moved upwards by a Boone KYC-22RC motor. The spring gauge (in grams) measures the force required to separate the disk from the dentifrice.

Cohesion tests are conducted as follows. The temperature of the toothpaste and effective parts of the apparatus are adjusted to 70°-80° F. They must remain within this temperature range while the test is being conducted.

The perforated sleeve of the base is raised and turned so that it remains elevated, resting on the small pin of the brass base plate. Approximately 15 grams of paste are squeezed from the tube. This material is used to fill the cup that is formed when the perforated sleeve is in the raised position. To fill the cup, paste ribbon is charged to the center and then worked toward the edge in a spiral design. The disk is then pressed evenly and firmly onto the paste, forcing excess through the holes in the sleeve. Sample thickness is determined by the height of three screw heads that are attached onto the disk. Next, the sleeve is turned around until it slips down and the pin of the base plate fits into the slot on the sleeve.

A hook at the bottom end of the spring gauge mechanism engages a ring at the top of the disk. No pull on the toothpaste sample is exerted initially. The scale indicator is adjusted to read 0. Then, the motor is started and allowed to run until the sample of paste separates. At that point the scale is read again. This reading is the toothpaste cohesion value, expressed in grams.

Calibration of the scale before and after a run is done with a 125 gram known weight. Adjustments are made to the spring gauge when necessary.

Sample Preparation

A set of dentifrices were prepared according to the following formulation.

| Component | % |
|---|---|
| Humectant (70% syrup) | 56.33 |
| Water | 14.04 |
| Syloid 63X | 10.0 |
| Syloid 244 | 9.0 |
| Polyethylene glycol (1500 M.W.) | 5.0 |
| Ethyl alcohol | 2.1 |
| Sodium lauryl sulfate | 1.6 |
| Peppermint oil | 1.0 |
| Sodium monofluorophosphate | 0.8 |
| Cellulose gum | 0.4 |
| Sodium saccharin | 0.3 |
| | 100.57* |

*About one-third of the alcohol is lost during processing.

Dentifrices according to the above formulation incorporating different humectants were evaluated for cohesion. The three humectants evaluated were a sorbitol solution, a hydrogenated starch hydrolyzate (Sample 2) and a solution of pure maltitol.

TABLE III

| Humectant | Grams of Cohesion |
|---|---|
| Sorbitol solution (70% sorbitol) | 160 |
| Maltitol solution (70% maltitol) | 160 |
| Sample 2 Polyol | 220 |

Reproducibility for the cohesion test is approximately ±5 grams. The results clearly indicate the cohesion superiority of the instant polyols relative to sorbitol and maltitol humectant systems.

EXAMPLE 7

Not only clear gel dentifrices but the more traditional opaque toothpastes can benefit from the use of the polyols herein described to improve textural properties. High cohesion can be achieved in opaque toothpastes, an illustration of which is cited below.

| Component | % |
|---|---|
| Polyol (Sample 2) | 15.0 |
| Calcium phosphate dihydrate, dibasic | 33.5 |
| Anhydrous calcium phosphate, dibasic | 5.0 |
| Titanium dioxide | 1.5 |
| Sodium lauryl phosphate | 1.5 |
| Carboxymethyl cellulose | 1.2 |
| Sodium monofluorophosphate | 0.8 |
| Peppermint oil | 0.6 |
| Sodium saccharin | 0.4 |
| Water | till 100 |

Having now fully described the invention, it will be apparent to one of ordinary skill in the art that many changes and modifications can be made thereto without departing from the spirit or scope of the invention as set forth herein.

What is claimed is:

1. A visually clear dentifrice composition comprising about 20 to 70% by weight of humectant solids, about 5 to 50% by weight of an abrasive, and water,
   (a) the humectant solids comprising a hydrogenated hydrolyzed polysaccharide wherein said hydrogenated hydrolyzed polysaccharide contains 25% or less maltitol and at least about 20 to 30% by weight $DP_{10}$ oligosaccharides or higher;
   (b) said abrasive being capable of:
      (i) cleaning and polishing human teeth without damaging said teeth, and of
      (ii) forming a clear gel when combined with the humectant system,
   (c) the amount of water and the distribution of the molecular weights of said hydrogenated hydrolyzed polysaccharide being such as to render the dentifrice composition translucent or transparent.

2. The composition of claim 1 wherein the hydrogenated hydrolyzed polysaccharide is provided by hydrogenating a polysaccharide composition, said hydrogenation yielding a polyol containing less than about 50% sorbitol.

3. The composition of claim 1 wherein the hydrogenated hydrolyzed polysaccharide is provided by hydrogenating a polysaccharide composition, said hydrogenation yielding a polyol containing less than about 30% sorbitol.

4. The composition of claim 1 wherein the hydrogenated hydrolyzed polysaccharide is provided by hydrogenating a polysaccharide composition, said hydrogenation yielding a polyol containing less than about 25% sorbitol.

5. The composition of claim 1 wherein said abrasive is present in an amount of 6 to 35% by weight.

6. The composition of claim 1 wherein said abrasive is present in an amount of 7 to 25% by weight.

7. The composition of claim 1 wherein said abrasive is selected from the group consisting of silica xerogels, and precipitated silicas.

8. The composition of claim 1 wherein said abrasive is silica xerogels.

9. The composition of claim 1 wherein said abrasive contains an average particle size between 2 and 30 microns.

10. The composition of claim 1 wherein said abrasive contains an average particle size between 3 and 15 microns.

11. The composition of claim 1 wherein said polysaccharide is starch.

12. The composition of claim 11 wherein said starch is derived from corn, potato, rice and wheat.

13. The composition of claim 12 wherein said starch is corn starch.

14. The composition of claim 1 wherein at least about 40% by weight of said hydrogenated hydrolyzed polysaccharide contains oligosaccharide with at least 3 glucose units.

15. The composition of claim 1 wherein at least about 50% by weight of said hydrogenated hydrolyzed polysaccharide contains oligosaccharide with at least 3 glucose units.

16. The composition of claim 1 containing substantially no glycerine.

17. The composition of claim 1 containing substantially no sorbitol.

18. The composition of claim 1 containing neither sorbitol nor glycerine.

19. The composition of claim 1 wherein the amount of water is about 10–50% by weight.

20. The composition of claim 1 wherein the amount of humectant solids is about 30 to 70% by weight.

21. A visually clear dentifrice composition comprising about 20 to 70% by weight of humectant solids, about 5 to 50% by weight of an abrasive, and water,
   (a) the humectant solids comprising a hydrogenated hydrolyzed polysaccharide wherein said hydrogenated hydrolyzed polysaccharide contains less than about 40% $DP_1$ and $DP_2$, no more than 25% $DP_2$, about 30 to 40% $DP_3$ through $DP_9$, and about 20 to 30% $DP_{10}$ or higher;
   (b) said abrasive being capable of:
      (i) cleaning and polishing human teeth without damaging said teeth, and of
      (ii) forming a clear gel when combined with the humectant system,
   (c) the amount of water and the distribution of the molecular weights of said hydrogenated hydrolyzed polysaccharide being such as to render the dentifrice composition translucent or transparent.

22. A method of cleaning and polishing teeth comprising treating said teeth with the dentifrice composition of any of claims 1 to 21.

23. An opaque dentifrice composition comprising about 5 to 70% by weight of humectant solids, about 5 to 50% by weight of an abrasive, and water, the humectant solids comprising a hydrogenated hydrolyzed polysaccharide wherein said hydrogenated hydrolyzed polysaccharide contains 25% or less maltitol and at least about 20 to 30% by weight $DP_{10}$ oligosaccharides or higher.

* * * * *

UNITED STATES PATENT AND TRADEMARK OFFICE
CERTIFICATE OF CORRECTION

PATENT NO. : 4,435,380
DATED : March 6, 1984
INVENTOR(S) : Morton Pader

It is certified that error appears in the above—identified patent and that said Letters Patent is hereby corrected as shown below:

Column 17, Example 7, line 25: delete the words "Sodium lauryl phosphate" and insert therefor the words -- Sodium lauryl sulfate --.

Signed and Sealed this

Twelfth Day of June 1984

[SEAL]

Attest:

GERALD J. MOSSINGHOFF

Attesting Officer　　　Commissioner of Patents and Trademarks